Figure 1:
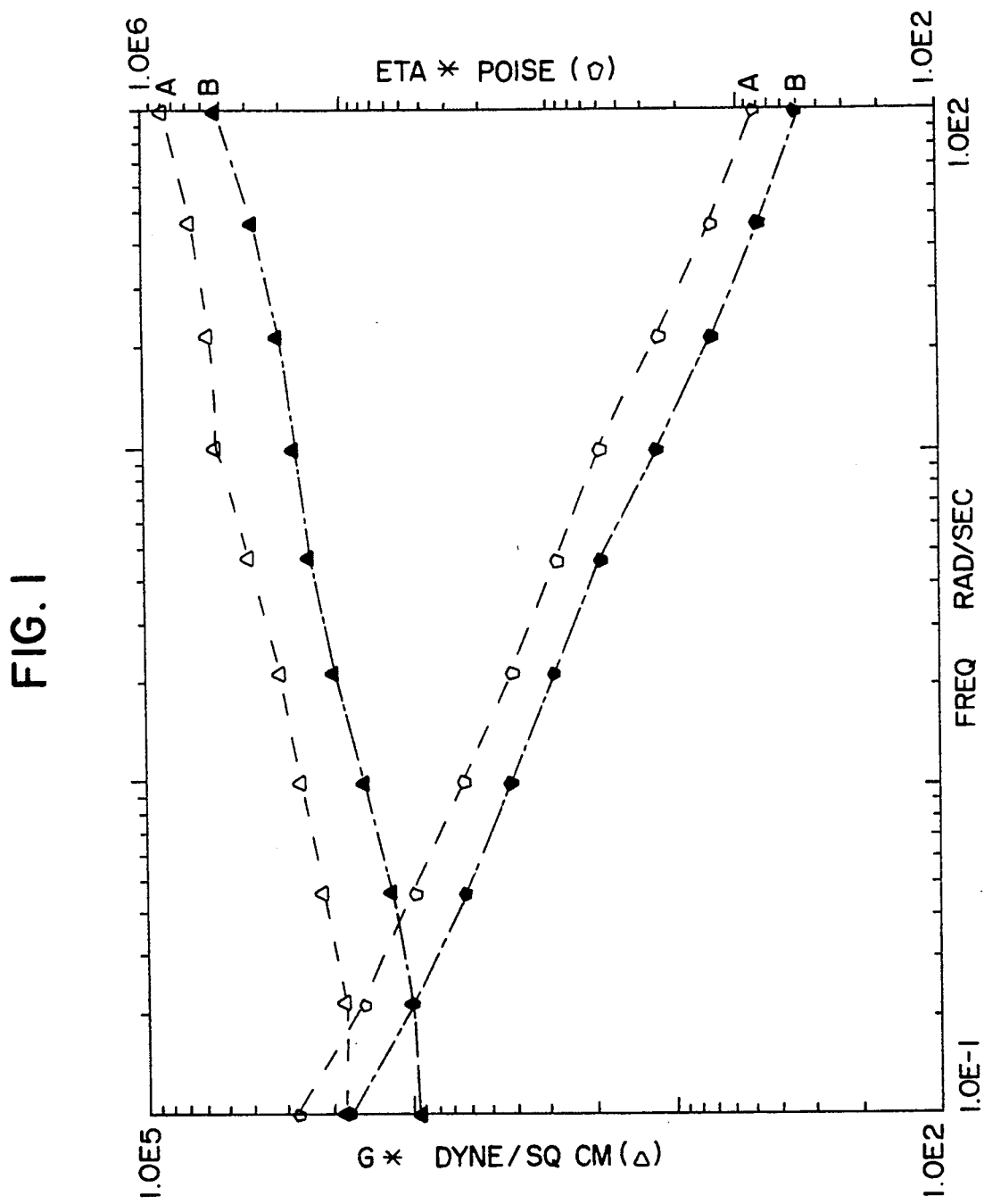
Figure 2:
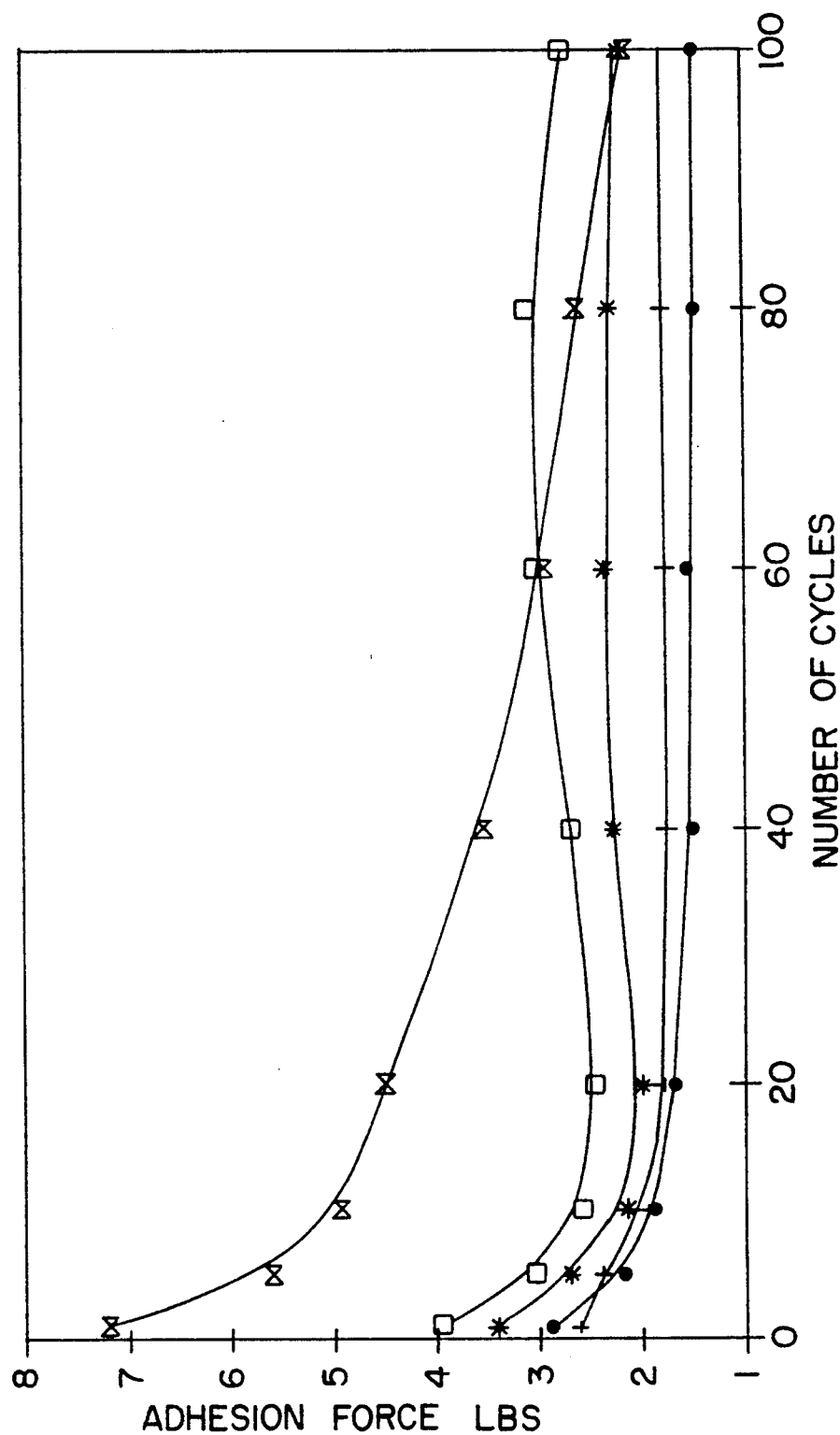

United States Patent [19]

Prosise et al.

[11] Patent Number: 5,266,624

[45] Date of Patent: Nov. 30, 1993

[54] HIGH LOAD POLYMER PASTES AS PHARMACEUTICAL ADHESIVES

[75] Inventors: William E. Prosise, Ramsey; Ki-Ho Chung, Oak Ridge, both of N.J.

[73] Assignee: ISP Investments Inc., Wilmington, Del.

[21] Appl. No.: 916,455

[22] Filed: Jul. 20, 1992

[51] Int. Cl.⁵ ............................................. C08L 91/00
[52] U.S. Cl. .................................. 524/313; 524/318; 523/118; 523/120
[58] Field of Search ............... 524/313, 318; 523/118, 523/120

[56] References Cited

U.S. PATENT DOCUMENTS

| | | | |
|---|---|---|---|
| 4,318,742 | 3/1982 | Lokken | 524/35 |
| 5,027,924 | 8/1991 | Tazi et al. | 523/118 |

*Primary Examiner*—Paul R. Michl
*Assistant Examiner*—LaVonda DeWitt
*Attorney, Agent, or Firm*—Marilyn J. Maue; Joshua J. Ward

[57] ABSTRACT

A high load ostial or odontologic adhesive composition containing a dispersion of an innocuous adhesive polymer in an oil base and between 0.01 and 5 wt. % of a hydrolyzable phospholipid, sufficient to form a paste or gel having high cohesive strength and conformity to a mucous membrane.

14 Claims, 2 Drawing Sheets

HIGH LOAD POLYMER PASTES AS PHARMACEUTICAL ADHESIVES

In one aspect this invention relates to an adhesive composition which contains high concentrations of an adhesive polymeric resin for added holding power while retaining a soft paste or gel-like consistency for easy pressure evacuation from a tube or flexible container. In another aspect, the invention relates to a highly moldable, non-sensitizing denture adhesive.

BACKGROUND OF THE INVENTION

Various ostial and odontologic adhesive compositions are described in the patent literature, for example see U.S. Pat. Nos. 5,037,924; 4,910,247; 4,318,742 and 4,393,080. Generally such compositions exhibit resistance to biological fluids, are non-irritating and have good adhesion over a limited period of time. However, it is generally desired to increase the resin content of the existing formulations to reinforce and extend the adhesive holding power while still retaining a viscosity which permits high conformity to the shape of the mucous membrane to which the adhesive is applied. Attempts to formulate compositions of smooth paste or gel-like consistency which contain up to 45 or 65% solids have not met with complete success since increase in resin content is invariably accompanied by an undesired increase in viscosity such that the paste-like and structure conforming properties are greatly diminished.

Accordingly, it is an object of this invention to overcome the above difficulties while still retaining the desirable properties of prior ostial and odontalgic adhesives.

Another object of the invention is to introduce a viscosity limiting compound into a commercial ostial or odontalgic formulations which permits marked increase, in polymer loading with minimal increase in composition viscosity.

Still another object is to provide a denture adhesive which is simple and economical to prepare.

These and other objects will become apparent from the following description and disclosure.

THE INVENTION

In accordance with this invention, it is now found that certain lipoids, when added to a non-toxic, adhesive polymer-containing, aqueous suspension or dispersion in an effective viscosity controlling amount, retain the paste or gel-like consistency of the formulation which is required in pharmaceutical adhesives while permitting considerable increase in the polymeric resin concentration to provide additional strength and lasting holding power.

The preferred lipoids employed as the viscosity limiting agents of this invention are hydrolyzable phospholipids which include lecithins, as defined in the Official Monograph of the United States Pharmacopeia, National Formulary XVII. The lecithins are derived from vegetable and animal sources. Examples of the hydrolyzable phospholipids include said lecithins, cephalin, a blend of phospholipids derived from egg yolk or vegetable oils, sphingomyclin, 1,2-diglyceride monosodium phosphate, 1-monoglyceride-3-monosodium phosphate and other phospholipids which can be hydrolyzed to yield phosphoric acid, an alcohol, a fatty acid and a nitrogenous base, e.g. choline or ethanol amine. Especially preferred of this group are lecithins having the formula

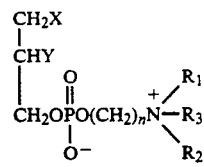

wherein each of X and Y is independently $C_1$ to $C_{22}$ acid ester or one of X and Y can be

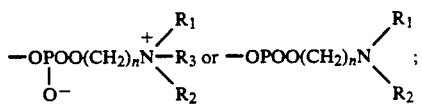

n has a value of from 1 to 6 and $R_1$, $R_2$ and $R_3$ are each independently lower alkyl ($C_1$ to $C_4$ alkyl) or hydrogen. Of these, the most preferred lecithins are those wherein the X and Y are —OCOR groups with R groups derived from the same or different fatty acid, e.g. stearic, palmitic, oleic, linolenic, linoleic acids or similar saturated or unsaturated fatty acids. It will be understood that a mixture of the present lipoids can be employed to provide the viscosity limiting function of this invention. Although individual lecithins, e.g. phosphatidyl choline, can be employed, mixtures of phosphatides are more readily available. An example of a soy lecithin is CENTROLEX-F having the following composition:

| wt. % | Component |
| --- | --- |
| 20–22 | phosphatidyl choline |
| 21–23 | phosphatidyl ethanol amine |
| 18–20 | phosphatidyl inositol |
| 4–8 | phosphatidic acid |
| 9–12 | glycol lipids and fatty acid ester derivatives of saturated and unsaturated fatty acids* |

*palmitic (15–18%), stearic (3–6%), oleic (9–11%), linoleic (56–60%) and linolenic (6–9%)

An example of an egg lecithin is OVATHIN having the following composition:

| wt. % | Component |
| --- | --- |
| 68–72 | phosphatidyl choline |
| 12–16 | phosphatidyl ethanol amine |
| 0–2 | phosphatidyl inositol |
| 2–4 | sphingomyeline |
| 10 | other phospholipids and fatty acid esters of saturated and unsaturated fatty acids* |

*palmitic (27–29%), stearic (14–17%), oleic (35–38%), linoleic (15–18%), linolenic (0–1%) and arachidonic (3–5%)

These and other hydrolizable animal or vegetable lecithins are suitably employed in the present invention, as well as other hydrolyzable lipoids such as triglycerol monostearate such as SANTONE 3-1-S; octaglycerol monooleate, e.g. SANTONE 8-1-0; triglycerol mixed with hydrogenated fatty acid esters, e.g. SANTONE 3-1-SH, and the like.

The phospholipid or an admixture thereof is added to the adhesive formulation in an amount between 0.01 and 5 wt. %; preferably in an amount between about 0.05 and about 1 wt. %, of the total composition. Generally the concentration of the lipoid or lipoid mixture with respect to polymer is between about 0.02 and about 10 wt. %, preferably between about 0.1 and about 2 wt. %; although higher concentrations of lipoids can be tolerated to achieve and maintain the desired viscosity in the formulation. Such inclusion of the phospholipid in the adhesive composition increases the polymer load potential by between about 3 and about 15% without raising the viscosity of the mixture. Thus, a stronger, time extended adhesive which resists deterioration by action of saliva and moisture is achieved. Additionally, the present phospholipid containing compositions can contain up to 70% solids in the form of a gel or soft pasty product.

The polymeric resins employed in the ostomic adhesives of the invention are any of those commercially available and include blends or mixtures of mixed or partial salts of maleic anhydride/acrylic copolymers, vinyl ether/maleic acid copolymers, vinyl ether/maleic acid/maleic anhydride terpolymers and or alkyl amino salts thereof, maleic anhydride/vinyl ether/isobutylene terpolymers, vinyl ether/maleic anhydride copolymer with hydroxylated compounds such as a polyethoxylated fatty alcohol, oleyl alcohol, nonyl phenol, octyl phenol, polyethylene glycol, propylene glycol and similar compounds and mixed salts of vinyl ether/maleic anhydride and stearic acid and the like, examples of which are to be found in U.S. Pat. Nos. 5,104,926, filed Dec. 22, 1989; 5,066,709, filed Sep. 20, 1990 and Ser. No. 786,638, now U.S. Pat. No. 5,147,941 filed Nov. 1, 1991, as well as in the U.S. patents referred to above in the discussion on the Background of the Invention.

The above polymeric resins are generally dispersed in a non-toxic oil base, such as white petrolatum, mineral oil, polyethylene wax, a microcrystalline wax, petroleum jelly, beeswax, benzoated lard, glycerine, whey, polyethylene or polypropylene glycols, zinc oxide eugenol paste, and the like. The weight ratio of oil base to polymer can vary over the range of from about 5:1 to about 1:5, depending on the desired thickness of the composition.

The composition may also contain various adjuvants such as flavoring agents, coloring agents, additional emulsifiers, thickeners, as well as innocuous preservatives such as hexamethylene tetramine, an alkyl or aryl ester of p-hydroxybenzoic acid, etc. which additives are incorporated in minor amounts, as described in the art. Also the composition may contain a humectant to assist moisture absorption of the adhesive dispersion. The present compositions are substantially anhydrous, although up to 10 wt. % water can be tolerated without detriment.

Representative of a useful adhesive formulation to which the present lipoids are added is the following.

|  | wt. % |
|---|---|
| Light mineral oil | 8–15 |
| White petrolatum | 20–25 |
| Natural gum or wax | 20–40 |
| Emulsifier | 0.5–1 |
| Polymer resin | 20–30 |
| Flavoring Agent | QS |
| Coloring Agent | QS |

The manner in which the present composition may be prepared is both economical and commercially feasible.

Generally, the present compositions are prepared by adding the phospholipid component to a melt of the oil base optionally containing other liquid adjuvants, such as coloring and/or flavoring agents. The melt is usually obtained at a temperature of from about 85° C. to about 200° C. and forms a liquid portion of the composition. Solid polymer resin and any thickening component which may be desired is separately dry blended to a uniform consistency, and is then added to the melt under agitation to form a uniform dispersion. Constant agitation is continued during cooling of the resulting dispersion so as to maintain the uniform distribution of the polymer in the oil base.

The mixing of solids with the melt is conducted at a temperature of between about 50° C. and about 180° C., preferably between about 70° C. and about 100° C. for a period of from about 8 minutes to about 5 hours or until a uniform smooth gel or paste consistency is achieved.

The resulting mixture is an anhydrous paste or gel which is easily extracted from a tube or other container in which it may be packaged.

Having thus generally described the invention, reference is now had to the following which illustrate preferred embodiments and comparative tests by way of examples but which are not to be construed as limiting to the scope of this invention as more broadly set forth above and in the appended claims.

EXAMPLES 1–14

The following compositions in Table I were prepared by forming a melt of mineral oil, white petrolatum, and lipoid emulsifier in a jacketed Hobart Mixer equipped with a paddle stirrer operating at about 300 rpm. Coloring and flavoring agents were then added to the melt and mixed therein until a uniform composition was achieved, usually within a period of from about 10 to 30 minutes.

Separately, the cellulose thickener and Gantrez MS-955D* were dry blended in a Paterson-Kelly V blender until a uniform composition was obtained, within a period of 10–15 minutes at about 80°–85° C., after which the dry blended mixture was gradually added to the melt over a period of 30 minutes under constant agitation at a temperature of about 70°–75° C. so as to obtain a uniform dispersion of solids in the melt. The resulting dispersion was then cooled to room temperature with cooling water under constant agitation. These compositions are reported in following Table I.

*Mixed Na and Ca salts of poly(methyl vinyl ether/maleic anhydride having a molecular weight of 600,000–1,500,000

TABLE I

| Composition | WEIGHT % | | | | | | | | | | | | | |
|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |
| Light Mineral Oil | 11.90 | 12.15 | 12.28 | 12.34 | 12.40 | 18.90 | 19.15 | 18.90 | 19.15 | 19.40 | 18.90 | 19.15 | 18.90 | 19.15 |
| White Petrolatum | 23.60 | 23.60 | 23.60 | 23.60 | 23.60 | 30.40 | 30.40 | 30.40 | 30.40 | 30.40 | 30.40 | 30.40 | 30.40 | 30.40 |
| Emulsifier |  |  |  |  |  |  |  |  |  |  |  |  |  |  |
| polyglycerol ester[3] | — | — | — | — | — | 0.50 | 0.25 | — | — | — | — | — | — | — |
| glycerol monostearate (GMS-90)[1] | — | — | — | — | — | — | — | 0.50 | 0.25 | — | — | — | — | — |

TABLE I-continued

| Composition | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| calcium stearoyl lactylate (VERV Ca)[2] | — | — | — | — | — | — | — | — | — | — | 0.50 | 0.25 | — | — |
| (Lecithin[4]) | 0.50 | 0.25 | 0.13 | 0.06 | — | — | — | — | — | — | — | — | 0.50 | 0.25 |
| Gantrez MS-955D | 26.00 | 26.00 | 26.00 | 26.00 | 26.00 | 26.00 | 26.00 | 26.00 | 26.00 | 26.00 | 26.00 | 26.00 | 26.00 | 26.00 |
| Cellulose thickener | | | | | | | | | | | | | | |
| hydroxypropylmethyl cellulose | 38.00 | 38.00 | 38.00 | 38.00 | 38.00 | — | — | — | — | — | — | — | — | — |
| carboxymethyl cellulose | — | — | — | — | — | 24.40 | 24.40 | 24.20 | 24.20 | 24.20 | 24.20 | 24.20 | 24.20 | 24.20 |
| Color and flavoring agents | QS | QS | QS | QS | QS | QS | QS | QS | QS | QS | QS | QS | QS | QS |

[1]supplied by Bredda Corp.
[2]supplied by Patco Corp.
[3]supplied by Durkee Foods
[4]CENTROLEX ® F supplied by Central Saya Co.

The above compositions were then evaluated for Tube Squeezability, i.e. a viscosity determination and for adhesion strength and results are reported in following Table II.

TUBE SQUEEZE TEST

The squeezable tube test was carried out as described by B. Noren in the Journal of the Society of Cosmetic Chemistry Volume 27, pages 47-61, 1976, entitled A METHOD TO EVALUATE THE TUBE SQUEEZING PROPERTIES OF TOOTHPASTE. Specifically, this test method comprises taking a 40 g. sample of the composition and filling a 1 inch diameter GLAMINATE ® tube (American National Can Corp.) having a 0.39 inch length and having a 0.168 inch diameter orifice. Then pressing the tube with a 1 inch circular piston exerting 20 psig for exactly 5.000 seconds. The grams of extruded sample were measured and recorded as shown in TABLE II.

INSTRON STUDIES FOR ADHESION

A small amount (~2 g. ) of denture adhesive is subjected to cyclic compressive and tensile stresses between two polymethylmethacrylate plates.

The first step in running this test is to bring the plates together to obtain the zero position (A). The upper plate is then raised 0.06 inch and the upper cycle limit on the Instron is set at this point (B). The upper plate is then lowered and the lower cycle limit is set (C). In its lowest position, then, the upper plate is 0.03 inch from the lower plate.

With these Instron settings determined, the upper plate was then raised high enough to spread 2 grams of sample uniformly over the top of the lower plate. Then 200 ml of simulated salivary fluid was added so that the sample was barely covered. The Instron crosshead was cycled between the set limits at a crosshead speed of 0.2 in./min. The Instron chart was set in the continuous mode at a speed of 2 in./min. to record the compression and adhesion force for each cycle up to 100 cycles.

At the end of 100 cycles, the upper plate motion was halted and the plate cleaned. The apparatus was thoroughly washed and dried in preparation for the next denture adhesive evalution.

The saliva solution was changed for each denture adhesive. Each recording was analyzed and the adhesional forces (lbs.) for the 1st, 5th, 10th, 15th . . . 100th cycles were recorded.

TABLE II

| Composition | Squeezability (g)[1] | Adhesion Strength lbs. at 100 cycles |
|---|---|---|
| 1 | 10.9 | 1.5 |
| 2 | 10.8 | 1.75 |

TABLE II-continued

| Composition | Squeezability (g)[1] | Adhesion Strength lbs. at 100 cycles |
|---|---|---|
| 3 | 8.3 | 2.3 |
| 4 | 8.8 | 2.8 |
| 5 | 3.4* | 2.2 |
| 6 | 14.0 | 0.5 |
| 7 | 14.0 | 0.5 |
| 8 | 13.0 | 0.5 |
| 9 | 12.0 | 0.3 |
| 10 | 6.0 | 0.1 |
| 11 | 15.0 | 0.4 |
| 12 | 14.5 | 0.2 |
| 13 | 15.8 | 0.4 |
| 14 | 15.6 | 0.4 |

*composition too thick - not squeezable
[1]grams of product squeezed from tube

RHEOLOGICAL CHARACTERIZATION

The dynamic rheological profile of the following adhesive methyl vinyl ether/maleic acid sodium and calcium salt compositions were compared and plotted on a log graph represented by FIGURE I.

| | COMPOSITION A* | COMPOSITION B** |
|---|---|---|
| Ca/Na salt of MVE/MA | 33.333 wt % | 33.333 wt % |
| white petrolatum | 66.667 wt % | 66.667 wt % |
| CENTROLEX-F | — | 0.5 wt % |

*designated by broken line - - - -
**designated by broken line — - — - — - —

In Figure I, G represents the complex mo represents the complex viscosity against the X axis angular frequency.

Dynamic measurements were performed at room temperature (25°±1° C.) to characterize the rheological properties of denture adhesive model systems. Rheometries Mechanical Spectrometer 800 with two 25 mm diameter parallel plates was used for the measurements.

In dynamic measurement, an oscillatory strain (sinusoidal strain) was applied on the sample and the response stress was measured, while in steady measurement one directional shear strain was applied on the sample and the response stress was measured. The dynamic measurements has many advantages: it is easy to run from low frequency to high frequency (wide range of time scale) and it does not destroy structure in the material because it applies very small amplitude of strain.

The stress dividied by strain was indicated by "modulus" and the stress divided by rate of strain was indicated in "viscosity". In dynamic experiment, the modulus and viscosity can be represented by complex number (or complex function) because stress and strain or rate of strain (all sinusoidal functions of time) are not necessarily in phase with one another. This is true for all viscoelastic materials and most of materials in nature (especially polymeric materials) are viscoelastic. The real or in-phase component of complex modulus is called "storage modulus", G', and is a measure of energy stored and recovered per cycle of sinusoidal deformation (elastic component of material). The imaginary or 90° out of phase component of complex modulus is called "loss modulus", G'', and is a measure of the energy dissipated or lost as heat per cycle of sinusoidal deformation (viscous component of material).

The real or in-phase component of complex viscosity is called "dynamic viscosity" related to the loss modulus by the equation $n' = G''/w$, where w is frequency in rad/sec. The dynamic viscosity is a function of frequency in essentially the same way that the steady shear viscosity is a function of shear rate. Therefore, the rheological profile obtained by dynamic measurement is analogous to rheological profile obtained from steady measurement.

FIGURE I illustrates the consistently lower complex modulus and complex viscosity over the entire frequency range with the B composition containing lecithin as compared to a composition without lecithin.

FIGURE II compares the adhesion force of denture adhesive compositions reported in Examples 1-5

■ represents 0.5% lecithin
+ represents 0.25% lecithin
* represents 0.125% lecithin
⋈ represents 0.0625% lecithin
  represents 0.0% lecithin This Figure shows that in the formulation with white petrolatum and light mineral oil, as little as about 0.06% lecithin is capable of controlling the viscosity in the adhesive.

In the above examples it is to be understood that other lecithins can be substituted for CENTROLEX-F e.g. OVATHIN or an individual lecithin e.g. phosphatidyl choline, to provide viscosity control of polymers.

What is claimed is:

1. An ostial or odontologic adhesive gel or paste composition comprising a substantially anhydrous dispersion containing between about 50 and about 70 wt. % solids of an innocuous adhesive polymer in an oil base and between 0.01 and 5 wt. % of a hydrolyzable lipoid.

2. The composition of claim 1 wherein said lipoid is a phospholipid.

3. The composition of claim 1 wherein said lipoid is selected from the group of triglycerol monostearate, octaglycerol monooleate and a mixture of triglycerol and a fatty acid ester.

4. The adhesive composition of claim 1 wherein the paste or gel contains between about 50 and about 65 wt. % solids.

5. The adhesive composition of claim 2 wherein the phospholipid is between about 0.05 and about 1 wt. % of the composition.

6. The adhesive composition of claim 5 wherein said phospholipid is a lecithin.

7. The adhesive composition of claim 6 wherein said lecithin has the formula

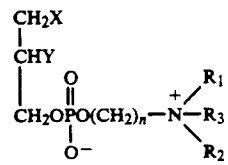

wherein each of X and Y is independently $C_1$ to $C_{22}$ acid ester or one of X and Y can be

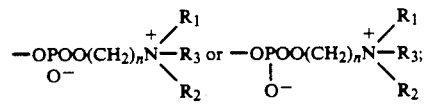

$R_1$, $R_2$ and $R_3$ are each individually $C_1$ to $C_6$ alkyl or hydrogen and n has a value of from 1 to 6.

8. The adhesive composition of claim 7 wherein X and Y are the same or a different fatty acid ester radical selected from the group consisting of stearate, palmitate, oleate, linoleate and linolenate.

9. The composition of claim 6 wherein the phospholipid is a mixture of lipoids.

10. The composition of claim 9 wherein the phospholipid is a composition of 20-22 wt. % phosphatidyl choline; 21-23 wt. % phosphatidyl ethanolamine; 18-20 wt. % phosphatidyl inositol; 4-8 wt. % phosphatidic acid and 9-12 wt. % glycolipids and fatty acid ester derivatives of saturated and unaturated fatty acids.

11. The composition of claim 9 wherein the phospholipid is a mixture of 68-72 wt. % phosphatidyl choline; 12-16 wt. % phosphatidyl ethanolamine; 0.2 wt. % phosphatidyl inositol; 2-4 wt. % sphingomyeline and 10 wt. % phospholipids and fatty acid esters of saturated and unsaturated fatty acids.

12. The composition of claim 1 wherein said polymer is methyl vinyl ether/maleic anhydride metal salt copolymer.

13. The composition of claim 1 wherein said polymer is polyethylene oxide.

14. The composition of claim 1 wherein said polymer is carboxymethyl cellulose.

* * * * *